US012580052B2

(12) United States Patent
Nakai et al.

(10) Patent No.: US 12,580,052 B2
(45) Date of Patent: Mar. 17, 2026

(54) SAMPLE ANALYSIS DEVICE, SAMPLE ANALYSIS METHOD, PHARMACEUTICAL ANALYSIS DEVICE AND PHARMACEUTICAL ANALYSIS METHOD

(71) Applicants: Shimadzu Corporation, Kyoto (JP); National Institute of Health Sciences, Kawasaki (JP)

(72) Inventors: Yusuke Nakai, Kyoto (JP); Eiichi Yamamoto, Ibaraki (JP)

(73) Assignees: SHIMADZU CORPORATION, Kyoto (JP); National Institute of Health Sciences, Kawasaki (JP)

( * ) Notice: Subject to any disclaimer, the term of this patent is extended or adjusted under 35 U.S.C. 154(b) by 363 days.

(21) Appl. No.: 18/116,055

(22) Filed: Mar. 1, 2023

(65) Prior Publication Data

US 2023/0317213 A1     Oct. 5, 2023

(30) Foreign Application Priority Data

Mar. 1, 2022    (JP) ................................. 2022-031302

(51) Int. Cl.
G16C 20/10       (2019.01)
G01N 33/15       (2006.01)

(52) U.S. Cl.
CPC ............. G16C 20/10 (2019.02); G01N 33/15 (2013.01)

(58) Field of Classification Search
CPC ........ G16C 20/10; G16C 20/70; G16C 20/30; G01N 33/15; G06N 7/01; G06N 20/00; G16H 70/40; G06F 30/20
See application file for complete search history.

(56) References Cited

U.S. PATENT DOCUMENTS

2003/0158670 A1*   8/2003   Hougaard .............. G16H 10/20
                  702/19
2009/0094059 A1*   4/2009   Coleman ................ G16C 20/30
                  705/2

(Continued)

FOREIGN PATENT DOCUMENTS

EP           3748639 A1    12/2020

OTHER PUBLICATIONS

"Assessment of stability test data for pharmaceutical products containing a new active ingredient," Japan Pharmaceutical Manufacturers Association and the Pharmaceutical Publishing Center, Mar. 2005, submitted with partial translation on pp. 22-23.

(Continued)

*Primary Examiner* — Manuel A Rivera Vargas
(74) *Attorney, Agent, or Firm* — Muir Patent Law, PLLC

(57) ABSTRACT

A sample analysis device includes an acquirer that acquires quantitative measurement information (measurement data) of a plurality of substances including a test substance present in a sample, an estimator that retrieves a reaction model stored in a storage device, models the test substance using the reaction model and provides the quantitative measurement information (measurement data) of the plurality of substances to the reaction model of the test substance to estimate a parameter of the reaction model, and a calculator that calculates quantitative estimation information of the test substance in any period of time or information in regard to a period of time until quantitative estimation information of the test substance reaches a predetermined threshold value, based on the parameter estimated by the estimator.

15 Claims, 12 Drawing Sheets

(56)                 References Cited

U.S. PATENT DOCUMENTS

| 2017/0199166 | A1 * | 7/2017 | Hong | ................. | G01N 30/8624 |
| 2020/0005176 | A1 * | 1/2020 | Imazawa | .................. | G06N 7/01 |
| 2022/0328139 | A1 | 10/2022 | Brass | | |
| 2024/0013869 | A1 * | 1/2024 | Kelly | .................... | G16C 60/00 |

OTHER PUBLICATIONS

WEB page for ASAPprime (a software package based on the Accelerated Stability Assessment Program), exact publication date unknown, searched on May 24, 2021, https://www.ms-scientific. com/products/lifescience/asapprime and its English Machine Translation.

Khawam et al. "Solid-State Kinetic Models: Basics and Mathematical Fundamentals", J. Phys. Chem. B, 110(35), 17315-17328, Aug. 15, 2006.

Wakiyama, "Drug stability and shelf life", Materials Life, vol. 3, No. 2, p. 104~109, Apr. 1991.

Office Action in the counterpart Japanese patent application 2022-031302, dated Dec. 9, 2025.

\* cited by examiner

F I G. 1
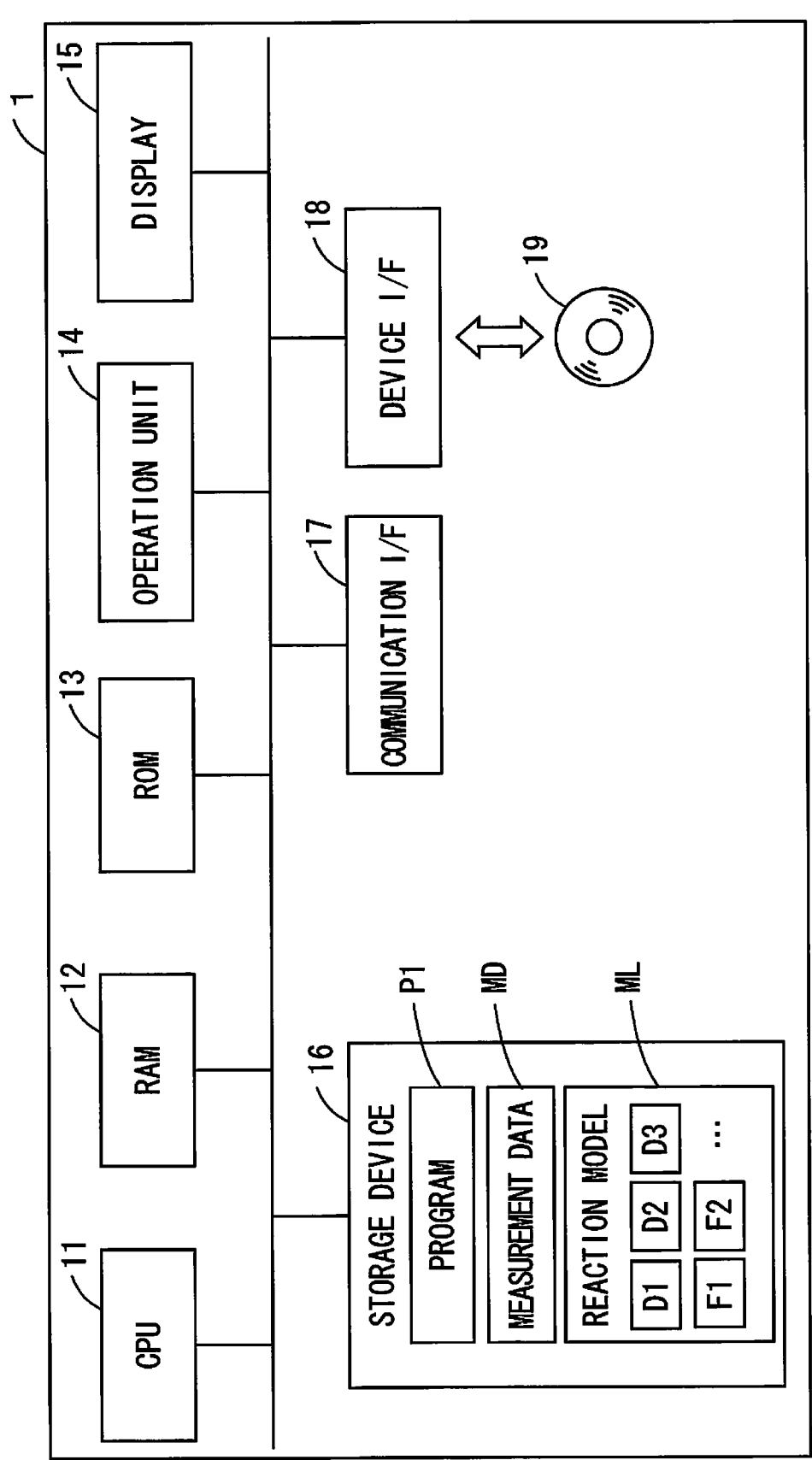

F I G. 2
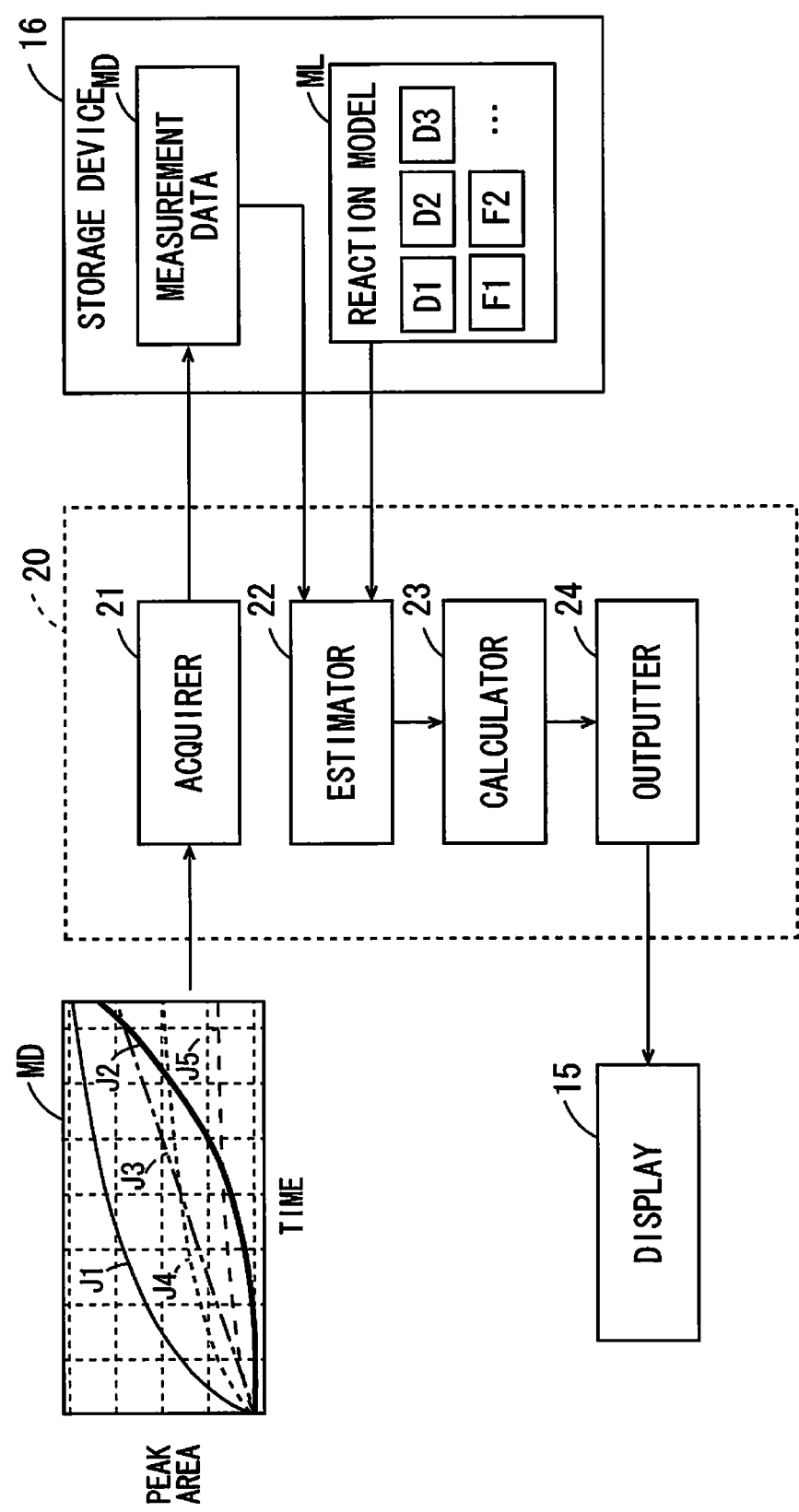

F I G.  3
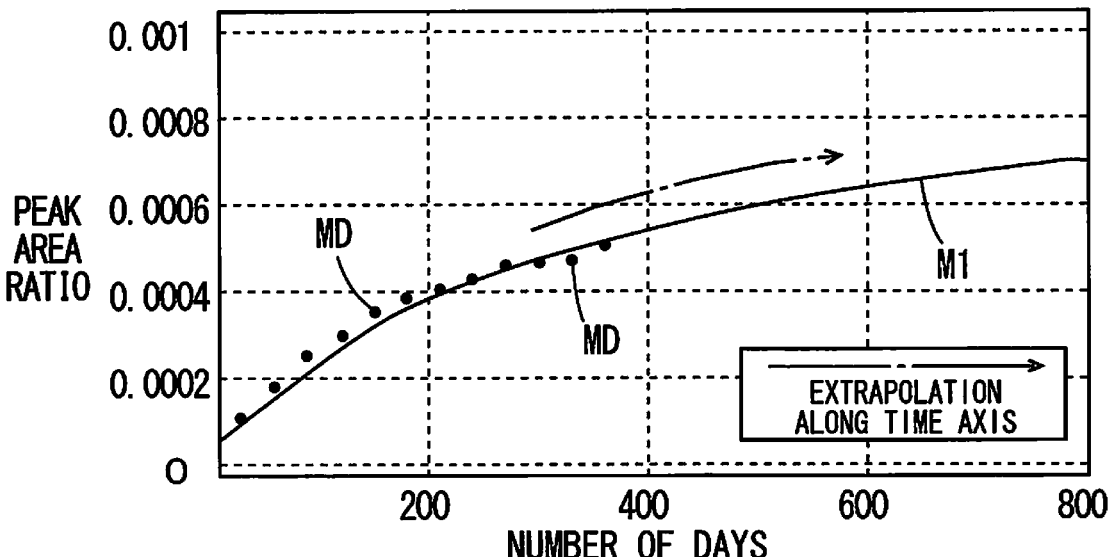

F I G. 4

| MODEL | DIFFERENTIAL FORM $f(\alpha)=(1/k)(d\alpha/dt)$ | INTEGRAL FORM $g(\alpha)=kt$ |
|---|---|---|
| P2 | $2\alpha^{1/2}$ | $\alpha^{1/2}$ |
| P3 | $3\alpha^{2/3}$ | $\alpha^{1/3}$ |
| P4 | $4\alpha^{3/4}$ | $\alpha^{1/4}$ |
| A2 | $2(1-\alpha)[-\ln(1-\alpha)]^{1/2}$ | $[-\ln(1-\alpha)]^{1/2}$ |
| A3 | $3(1-\alpha)[-\ln(1-\alpha)]^{2/3}$ | $[-\ln(1-\alpha)]^{1/3}$ |
| A4 | $4(1-\alpha)[-\ln(1-\alpha)]^{3/4}$ | $[-\ln(1-\alpha)]^{1/4}$ |
| B1 | $\alpha(1-\alpha)$ | $\ln[\alpha/(1-\alpha)]+c^{\alpha}$ |
| R2 | $2(1-\alpha)^{1/2}$ | $1-(1-\alpha)^{1/2}$ |
| R3 | $3(1-\alpha)^{2/3}$ | $1-(1-\alpha)^{1/3}$ |
| D1 | $1/(2\alpha)$ | $\alpha^{2}$ |
| D2 | $-[1/\ln(1-\alpha)]$ | $((1-\alpha)\ln(1-\alpha))+\alpha$ |
| D3 | $[3(1-\alpha)^{2/3}]/[2(1-(1-\alpha)^{1/3})]$ | $(1-(1-\alpha)^{1/3})^{2}$ |
| D4 | $3/[2((1-\alpha)^{-1/3}-1)]$ | $1-(2/3)\alpha-(1-\alpha)^{2/3}$ |
| F0/R1 | $1$ | $\alpha$ |
| F1 | $(1-\alpha)$ | $-\ln(1-\alpha)$ |
| F2 | $(1-\alpha)^{2}$ | $[1/(1-\alpha)]-1$ |
| F3 | $(1-\alpha)^{3}$ | $(1/2)[(1-\alpha)^{-2}-1]$ |

F I G.  6
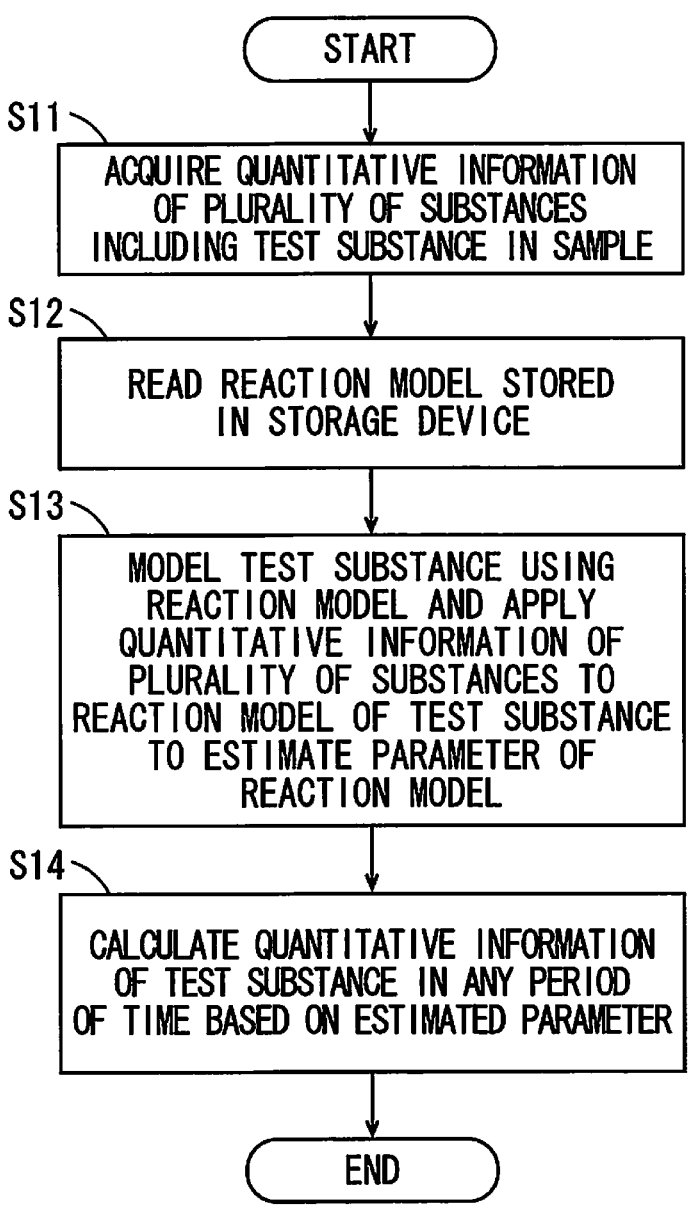

F I G. 7
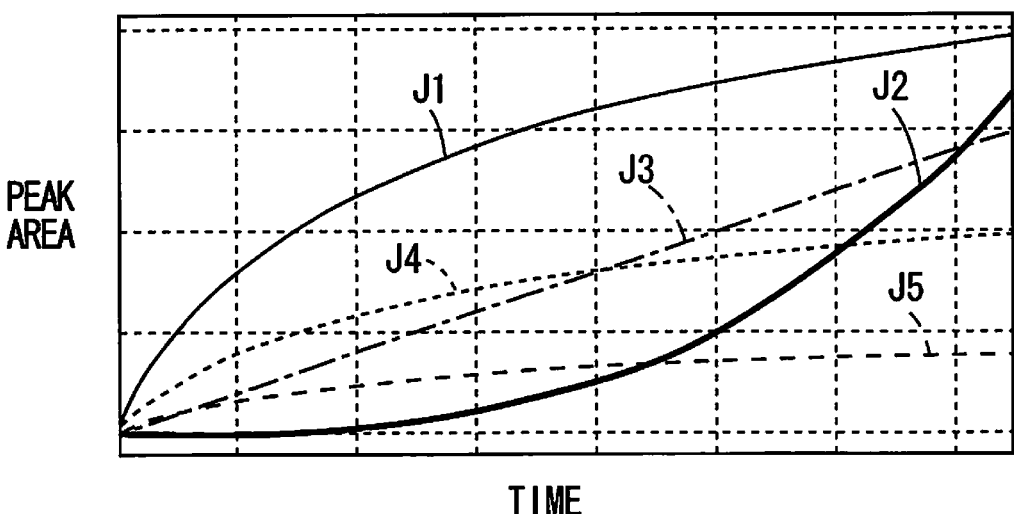

F I G. 8
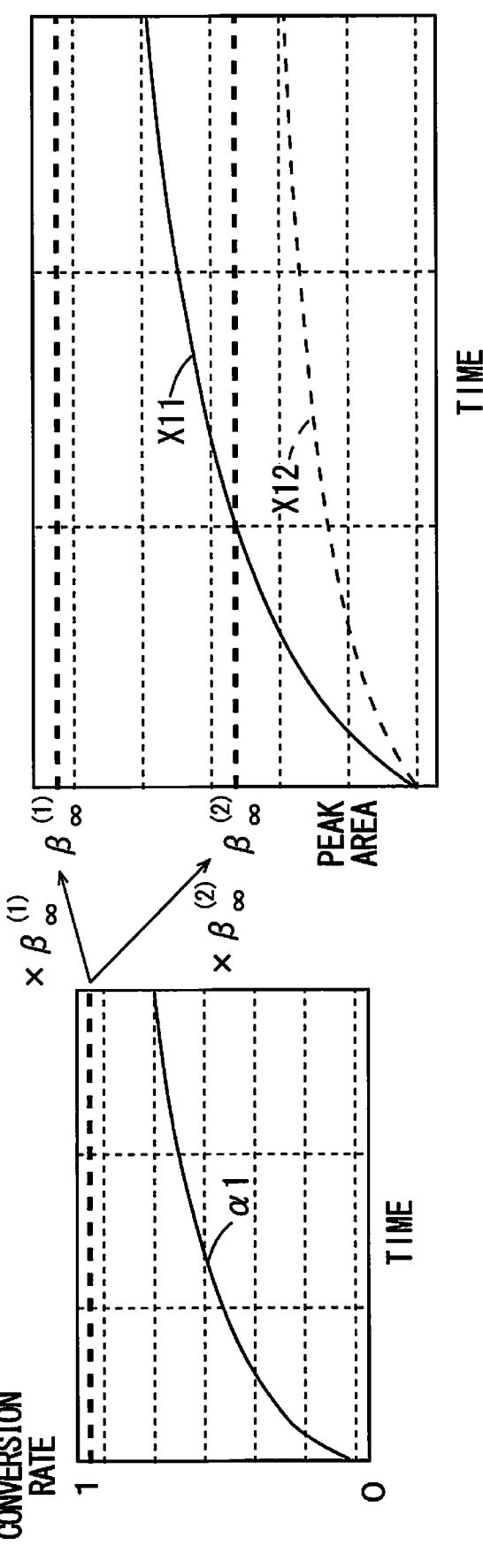

F I G.  9
TEMPORAL CHANGE OF PEAK AREA RATIO OF EACH IMPURITY
(25°C60%RH)
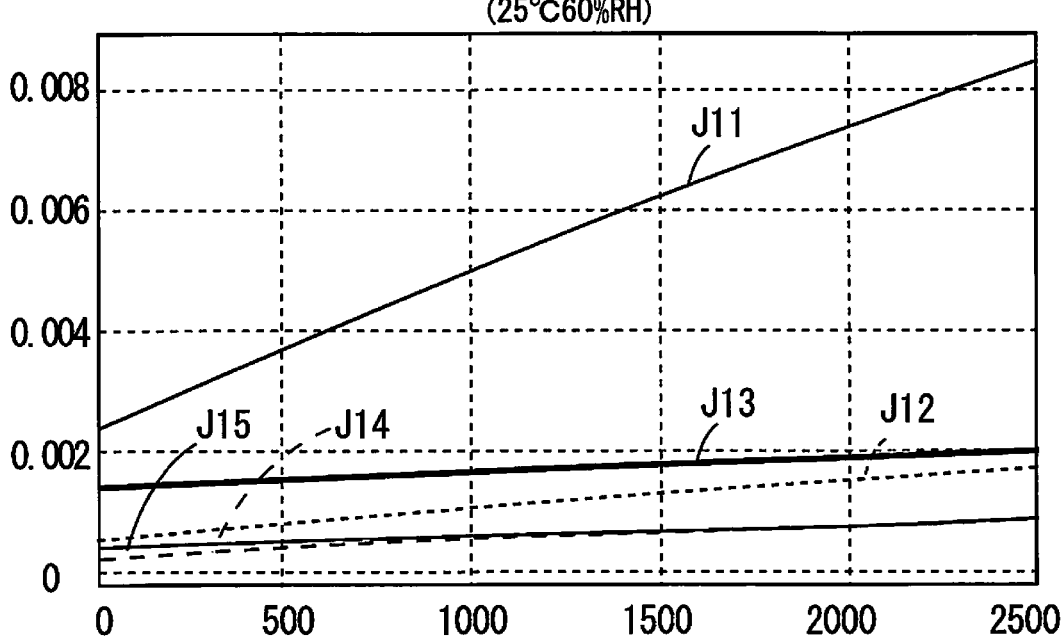
F I G.  1 0
SIMULATION DATA IN REGARD TO FIVE IMPURITIES OBTAINED
BY SIMULATION OF SILODOSIN
(11 POINTS IN TIME, 6 CONDITIONS OF TEMPERATURE
AND HUMIDITY, 330 POINTS)

F I G.  1 1
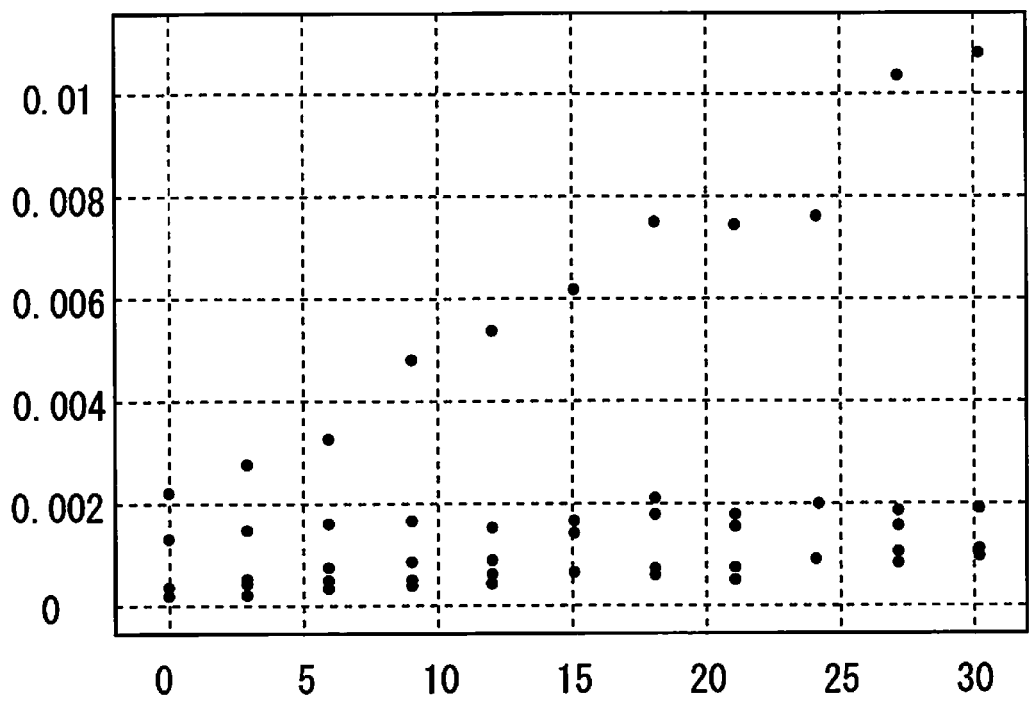
SIMULATION DATA IN REGARD TO FIVE IMPURITIES OBTAINED
BY SIMULATION OF SILODOSIN
(DATA FOR 11 POINTS IN TIME, ONE CONDITION OF 60°C
AND 50%RH IS EXTRACTED.)

F I G.  1 2
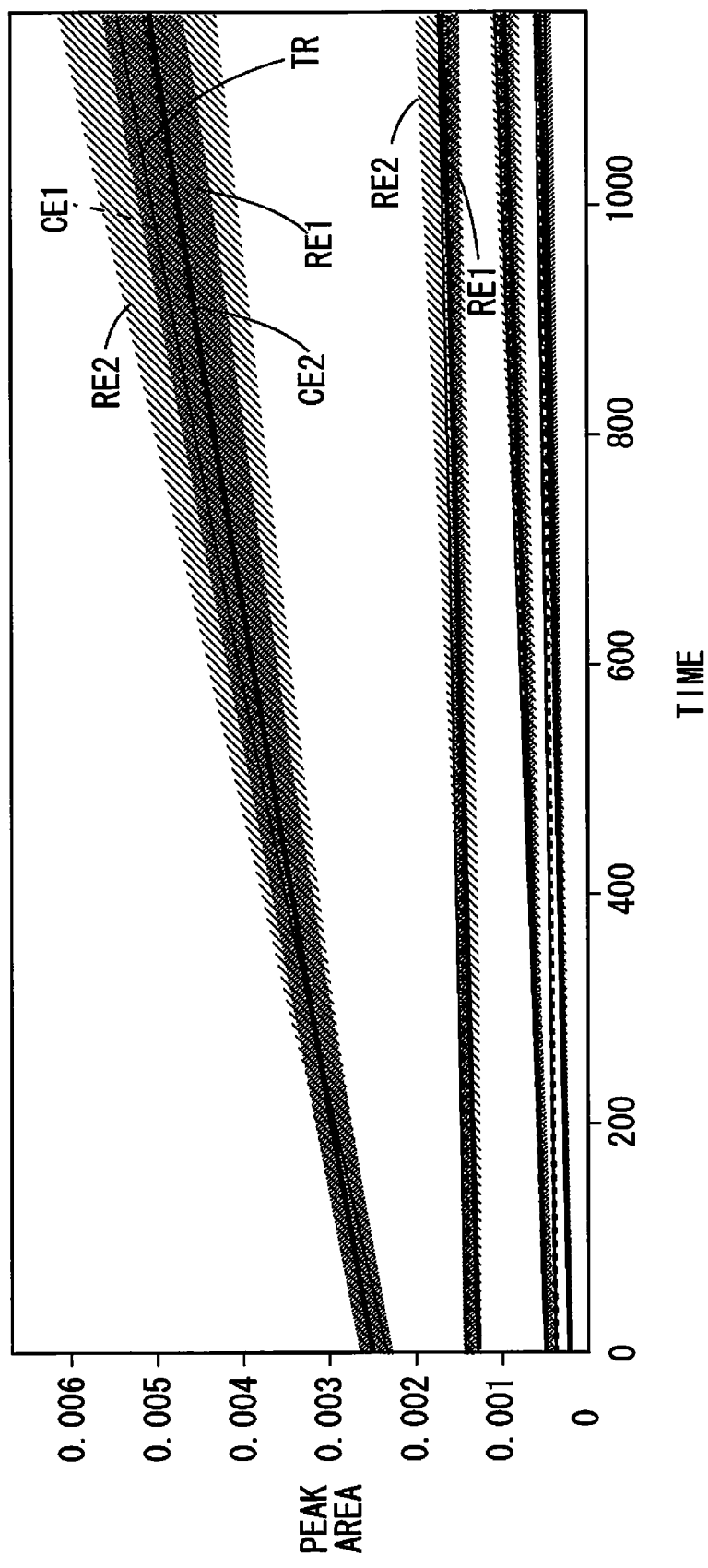

F I G .   1 3

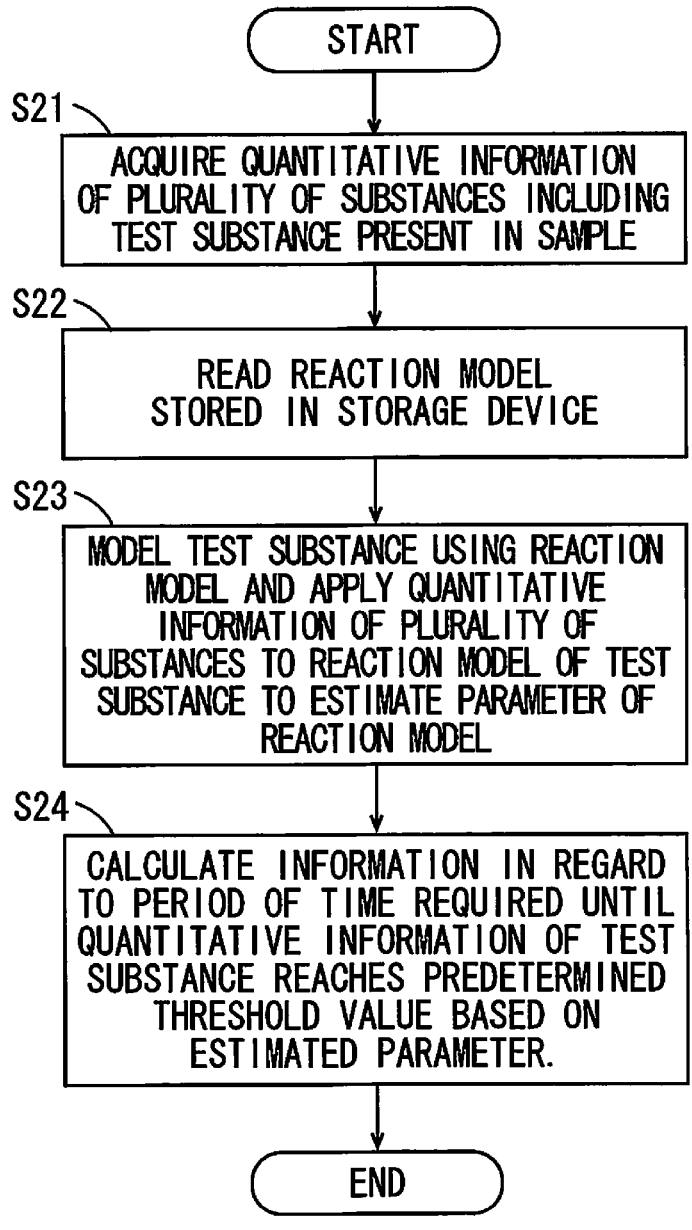

START

S21 — ACQUIRE QUANTITATIVE INFORMATION OF PLURALITY OF SUBSTANCES INCLUDING TEST SUBSTANCE PRESENT IN SAMPLE

S22 — READ REACTION MODEL STORED IN STORAGE DEVICE

S23 — MODEL TEST SUBSTANCE USING REACTION MODEL AND APPLY QUANTITATIVE INFORMATION OF PLURALITY OF SUBSTANCES TO REACTION MODEL OF TEST SUBSTANCE TO ESTIMATE PARAMETER OF REACTION MODEL

S24 — CALCULATE INFORMATION IN REGARD TO PERIOD OF TIME REQUIRED UNTIL QUANTITATIVE INFORMATION OF TEST SUBSTANCE REACHES PREDETERMINED THRESHOLD VALUE BASED ON ESTIMATED PARAMETER.

END

SAMPLE ANALYSIS DEVICE, SAMPLE ANALYSIS METHOD, PHARMACEUTICAL ANALYSIS DEVICE AND PHARMACEUTICAL ANALYSIS METHOD

BACKGROUND

Technical Field

The present invention relates to a sample analysis device and a sample analysis method for analyzing a test substance included in a sample, and a pharmaceutical analysis device and a pharmaceutical analysis method for analyzing an active ingredient, an impurity or the like included in a formulation or the like.

Description of Related Art

A stability test is carried out to assess the temporal change of a pharmaceutical. In this test, a period (effective period) in which it can be ensured that the value of an active ingredient of a pharmaceutical is in a reference range or that the value of an impurity is equal to or smaller than a reference value is calculated. Generally, an active ingredient or an impurity is identified and quantified by liquid chromatography in regard to a pharmaceutical stored for a certain period in a thermo-humidistat chamber or the like, and the effective period is calculated based on the result.

It is necessary to store a pharmaceutical for a long period to carry out the stability test. In order to shorten this period, a method of predicting an effective period by using a reaction model function (extrapolation along a time axis) or a method of predicting an effective period under a low temperature (low humidity) condition based on a decomposition amount under a high temperature (high humidity) condition by using the Arrhenius equation (extrapolation along a temperature axis) is performed. Extrapolation along a time axis is disclosed in "Assessment of stability test data for pharmaceutical products containing a new active ingredient" published by Japan Pharmaceutical Manufacturers Association and the Pharmaceutical Publishing Center in March, 2005, for example. Extrapolation along a humidity axis is disclosed in the "WEB page for ASAPprime (a software package based on the Accelerated Stability Assessment Program)," by FreeThink Technologies, Inc., [Searched on May 24, 2021], <URL:https://www.ms-scientific.com/products/lifescience/asapprime>, for example.

SUMMARY

In order to predict the effective period of a pharmaceutical with use of a reaction model, measurement data of the pharmaceutical stored for a certain period is necessary. In a case in which the number of data points of the acquired measurement data is small, a parameter of a reaction model may not be estimated with high accuracy. Further, since the measurement data of a subtle amount of an impurity may have a poor S/N ratio, a parameter of a reaction model may not be estimated with high accuracy. When the estimation accuracy of the parameter of the reaction model is degraded, the effective period of a pharmaceutical is not predicted with high accuracy.

An object of the present invention is to provide a sample analysis device, a sample analysis method, a pharmaceutical analysis device and a pharmaceutical analysis method that enable highly accurate estimation of a parameter of a reaction model.

A sample analysis device according to one aspect of the present invention includes an acquirer that acquires quantitative measurement information of a plurality of substances including a test substance present in a sample, an estimator that retrieves a reaction model stored in a storage device, models the test substance using the reaction model and provides the quantitative measurement information of the plurality of substances to the reaction model of the test substance to estimate a parameter of the reaction model, and a calculator that calculates quantitative estimation information of the test substance in any period of time based on the parameter estimated by the estimator.

A sample analysis device according to another aspect of the present invention includes an acquirer that acquires quantitative measurement information of a plurality of substances including a test substance present in a sample, an estimator that retrieves a reaction model stored in a storage device, models the test substance using the reaction model and provides the quantitative measurement information of the plurality of substances to the reaction model of the test substance to estimate a parameter of the reaction model, and a calculator that calculates information in regard to a period of time until quantitative estimation information of the test substance reaches a predetermined threshold value based on the parameter estimated by the estimator.

The present invention is also directed to a sample analysis method, a pharmaceutical analysis device and a pharmaceutical analysis method.

Other features, elements, characteristics, and advantages of the present disclosure will become more apparent from the following description of preferred embodiments of the present disclosure with reference to the attached drawings.

BRIEF DESCRIPTION OF THE DRAWING

FIG. 1 is a diagram showing the configuration of a sample analysis device according to the present embodiment;

FIG. 2 is a block diagram showing the functions of the sample analysis device according to the present embodiment;

FIG. 3 is a diagram showing the extrapolation along a time axis;

FIG. 4 is a diagram showing an example of a reaction model;

FIG. 6 is a flowchart showing a simultaneous estimation method according to an embodiment; and FIG. 7 is a diagram showing the profiles of a plurality of impurities included in a sample;

FIG. 8 is a diagram showing the conversion from a conversion rate to a peak area;

FIG. 9 is a diagram showing the simulation data;

FIG. 10 is a diagram showing the simulation data;

FIG. 11 is a diagram showing the simulation data;

FIG. 12 is a diagram showing a result of estimation based on simulation data; and FIG. 13 is a flowchart showing a simultaneous estimation method according to a modified example of the embodiment.

DETAILED DESCRIPTION

Figure 5:
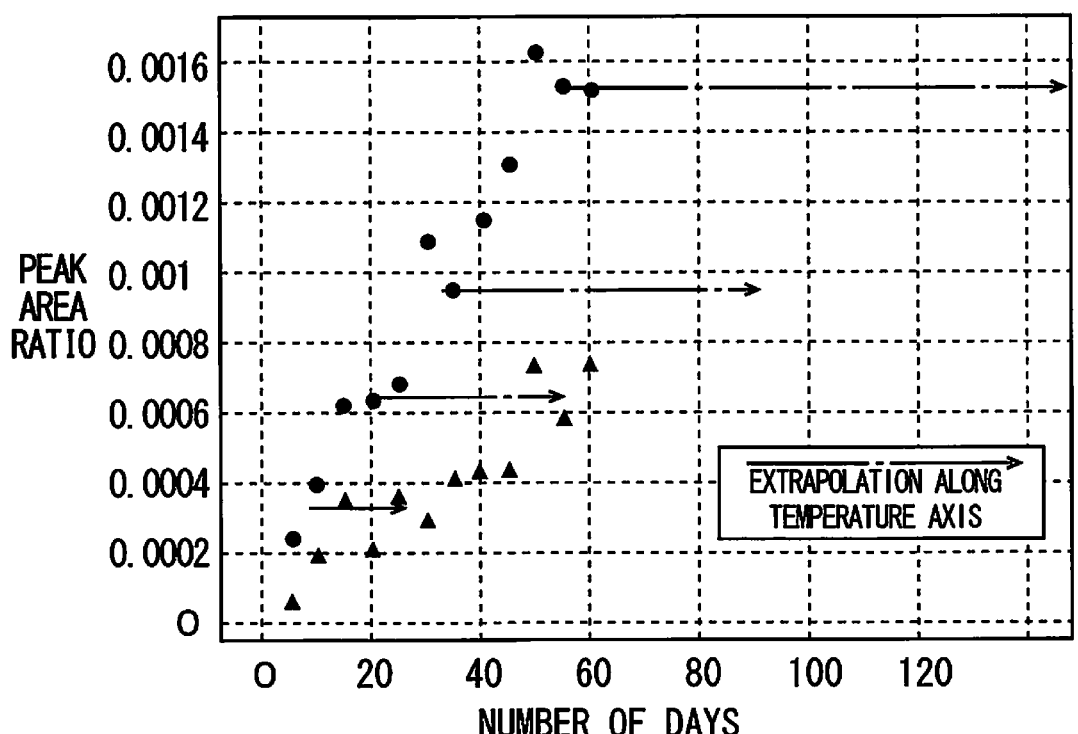
FIG. 5 is a diagram showing the extrapolation along a temperature axis.

A sample analysis device, a sample analysis method, a pharmaceutical analysis device and a pharmaceutical analysis method according to embodiments of the present invention will now be described with reference to the attached drawings.

(1) Configuration of Sample Analysis Device

FIG. 1 is a diagram showing the configuration of the sample analysis device 1 according to embodiments. The sample analysis device 1 of the present embodiment acquires measurement data MD of a sample obtained in a liquid chromatograph, a gas chromatograph, a mass spectrometer or the like. The measurement data MD has quantitative measurement information of a plurality of substances including a test substance present in a sample. Specifically, the measurement data MD includes data in regard to a peak area, a peak area ratio and the like of a plurality of substances including a test substance present in a sample. In the present embodiment, in particular, a pharmaceutical (a formulation or a drug substance) is used as a sample, by way of example. Specifically, in the present embodiment, the measurement data MD includes data in regard to a peak area of each of a plurality of substances included in a pharmaceutical, data in regard to the ratio of a peak area of an impurity with respect to a peak area of an active ingredient included in a pharmaceutical, or the like. The measurement data MD has the quantitative measurement information of a plurality of substances in regard to a plurality of points in time.

The sample analysis device 1 of the present embodiment is constituted by a personal computer. As shown in FIG. 1, the sample analysis device 1 includes a CPU (Central Processing Unit) 11, a RAM (Random Access Memory) 12, a ROM (Read Only Memory) 13, an operation unit 14, a display 15, a storage device 16, a communication interface (I/F) 17 and a device interface (I/F) 18.

The CPU 11 controls the sample analysis device 1 as a whole. The RAM 12 is used as a work area for execution of a program by the CPU 11. Various data, a program and the like are stored in the ROM 13. The operation unit 14 receives an input operation performed by a user. The operation unit 14 includes a keyboard, a mouse, etc. The display 15 displays information such as a result of analysis. The storage device 16 is a storage medium such as a hard disk. A program P1, the measurement data MD, a reaction model ML (data defining a reaction model function) are stored in the storage device 16.

The program P1 models a test substance using a selected reaction model and provides the quantitative measurement information of a plurality of substances to the reaction model to estimate a parameter of the reaction model. Further, the program P1 calculates the quantitative estimation information of the test substance in any period of time based on the estimated parameter. Further, the program P1 calculates the information in regard to a period of time until the quantitative estimation information of the test substance reaches a predetermined threshold value based on the estimated parameter.

The communication interface 17 is an interface that communicates with another computer through wireless or wired communication. The device interface 18 is an interface that accesses a storage medium 19 such as a CD, a DVD or a semiconductor memory.

(2) Functional Configuration of Sample Analysis Device

FIG. 2 is a block diagram showing the functional configuration of the sample analysis device 1. In FIG. 2, a controller 20 is a function that is implemented by execution of the program P1 by the CPU 11 while the CPU 11 uses the RAM 12 as a work area. The controller 20 includes an acquirer 21, an estimator 22, a calculator 23 and an outputter 24. That is, the acquirer 21, the estimator 22, the calculator 23 and the outputter 24 are the functions implemented by execution of the program P1. In other words, each of the functions 21 to 24 is a function included in the CPU 11.

The acquirer 21 receives the measurement data MD. The acquirer 21 receives the measurement data MD from another computer, an analysis device or the like via the communication interface 17, for example. Alternatively, the acquirer 21 receives the measurement data MD stored in the storage medium 19 via the device interface 18.

The estimator 22 models a test substance using a reaction model and provides the measurement data MD of a plurality of substances to the reaction model to estimate a parameter of the reaction model.

The calculator 23 calculates the quantitative estimation information of a test substance in any period of time based on the parameter estimated by the estimator 22. The quantitative estimation information includes a quantitative value, a confidence interval or a quantile of the test substance in any period of time. The calculator 23 also calculates the information in regard to a period of time until the quantitative estimation information of the test substance reaches a predetermined threshold value based on the parameter estimated by the estimator 22. The information in regard to a period of time includes a period of time, a confidence interval or a quantile until the quantitative estimation information of a test substance reaches a predetermined threshold value.

The outputter 24 causes the quantitative estimation information of the test substance to be displayed on the display 15. The outputter 24 also causes the information in regard to a period of time until the quantitative estimation information of the test substance reaches the predetermined threshold value to be displayed on the display 15.

The program P1 is stored in the storage device 16, by way of example. In another embodiment, the program P1 may be provided in the form of being stored in the storage medium 19. The CPU 11 may access the storage medium 19 via the device interface 18 and may store the program P1 stored in the storage medium 19 in the storage device 16 or the ROM 13. Alternatively, the CPU 11 may access the storage medium 19 via the device interface 18 and may execute the program P1 stored in the storage medium 19.

(3) Prediction Based on Measurement Data (3-1) Extrapolation Along Time Axis

Extrapolation along a time axis based on the measurement data MD which is the basis for performing the analysis method of the present embodiment will be described before description of an analysis method performed by the sample analysis device 1 of the present embodiment. FIG. 3 is a diagram showing the extrapolation along a time axis. In FIG. 3, the abscissa indicates the number of days (a period of time), and the ordinate indicates the ratio of a peak area of an impurity with respect to a peak area of a main component. In case of a pharmaceutical used as an example, the ordinate indicates the ratio of a peak area of an impurity with respect to a peak area of an active ingredient.

In FIG. 3, the plotted points indicate the measurement data MD. The measurement data MD is the data of the peak area ratios acquired on a plurality of days. In the example of FIG. 3, the measurement data MD is the data acquired from the first day to about the 400th day. Regression is performed on the acquired measurement data MD, so that a model M1 shown in the diagram is fitted. The model M1 is fitted, so that the peak area ratios on the future days such as the 600th day or the 800th day are estimated based on the measurement data MD of up to about the 400th day. The model M1 is fitted in this manner, so that the peak area ratio is extrapolated along the time axis. Similarly, it is possible to interpolate the peak area ratio along the time axis by fitting the model M1.

FIG. 4 is a diagram showing an example of a reaction model. In FIG. 4, each reaction model is represented in two forms: a differential form and an integral form. In the diagram, a represents a conversion rate, which is a value from 0 to 1 indicating the progress of reaction. k represents a reaction rate constant. It is possible to perform extrapolation (and interpolation) along the time axis by applying any reaction model to the measurement data MD and estimating a parameter such as k using regression. In a case in which regression is performed with use of a differential form, it is necessary to modify a differential form into $d\alpha/dt = kf(\alpha)$ to solve a differential equation. However, a differential form is characterized that it is easier to generalize a model formula with use of a differential form than with an integral form.

As specific examples, it has been known from experiments that the reaction between manganese oxide and sodium carbonate follows a D4 model in the table shown in FIG. 4, that the decomposition of a cadmium complex follows an F0 model, that the thermal oxidation of porous silicon and the desorption of 2-phenylethylamine (PEA) from a silica surface follow an F1 model, etc. Further, it has been known that there are many patterns in which the rate of auto-oxidation that naturally occurs in air increases in an accelerated manner, and it is conceivable that these patterns are modeled with use of a Power law model (Pn system), an Avrami model (An system) or the like that is obtained when an accelerated reaction is modeled. Examples of drugs that are to be auto-oxidized include vitamins such as ascorbic acid and riboflavin. The Power law model corresponds to P2 to P4 models, and the Avrami model corresponds to A2 to A4 models, in the table of FIG. 4.

(3-2) Extrapolation Along Temperature Axis

Subsequently, extrapolation along a temperature axis based on the measurement data MD which is the basis for performing the analysis method of the present embodiment will be described. FIG. 5 is a diagram showing the extrapolation along a temperature axis. In FIG. 5, the abscissa indicates the number of days, and the ordinate indicates the ratio of a peak area of an impurity with respect to a peak area of a main component. In case of a pharmaceutical used as an example, the ordinate indicates the ratio of a peak area of an impurity with respect to a peak area of an active ingredient.

Similarly to FIG. 3, the plotted points are also the measurement data MD and the data of the peak area ratios acquired on a plurality of days in FIG. 5. In FIG. 5, the black dots indicate the measurement data MD acquired under high temperature conditions (severe conditions), and the black triangles indicate the measurement data MD acquired under low temperature conditions (normal storage conditions). In the example of FIG. 5, the measurement data MD acquired under either high temperature conditions or low temperature conditions is the data acquired from the first day to about the 60th day. Further, it is possible to predict the data to be acquired under low temperature conditions based on the measurement data MD acquired under high temperature conditions by using the Arrhenius equation, described below. Thus, the peak area ratios to be acquired on the future days such as the 100th day, the 200th day, after 1 year and after 2 years under low temperature conditions (normal storage condition) are estimated. In this manner, the peak area ratios are extrapolated along the temperature axis. Although the extrapolation along the temperature axis is described, the similar method is also performed in regard to extrapolation along a humidity axis.

(3-3) Specific Processing of Extrapolation

Specific processing contents of the extrapolation along the time axis, the temperature axis and the humidity axis will be described. First, any reaction model is applied to a substance (an active ingredient or an impurity) included in a pharmaceutical having a conversion rate of $\alpha(t)$. Then, the measurement data MD obtained when the pharmaceutical is stored for a period t is provided to a reaction model, and a reaction rate constant k is estimated. This enables extrapolation along the time axis in regard to the measurement data MD. For example, a value of a parameter that accurately fits the measurement data MD is obtained by a regression analysis for estimation. Alternatively, the distribution of a parameter is obtained with use of Bayesian inference for estimation. Similarly to a reaction model $f(\alpha)=(1-\alpha)^n$ obtained when the reaction models F1 to F3 shown in FIG. 4 are generalized, in a case in which another parameter is included in a reaction model, the parameter is also to be estimated.

In a case in which extrapolation along the temperature axis and the humidity axis is considered in addition to extrapolation along the time axis, a modified Arrhenius equation (formula 1) is used.

[Formula 1]

$$k(T, H) = A\exp\left(-\frac{E}{RT} + B \times H\right) \tag{1}$$

In the formula 1, T represents an absolute temperature, H represents a relative humidity, A represents a frequency factor, E represents an activation energy, R represents a gas constant ($\approx 8.314$ J/(K·mol)) and B represents a parameter in regard to humidity. The formula 1 expresses the influence of temperature or humidity on the reaction rate constant k. When the formula 1 is substituted $f(\alpha)=(1/k)\cdot(d\alpha/dt)$ or $g(\alpha)=kt$ shown in FIG. 4, the formulas 2 and 3 are obtained.

[Formula 2]

$$f(\alpha(t, T, H)) = \frac{1}{A\exp\left(-\frac{E}{RT} + B \times H\right)} \frac{d\alpha}{dt} \tag{2}$$

[Formula 3]

$$g(\alpha(t, T, H)) = A\exp\left(-\frac{E}{RT} + B \times H\right)t \tag{3}$$

Then, one of the reaction models shown in FIG. 4 is applied to the formula 2 or the formula 3. Then, the measurement data MD obtained when a pharmaceutical having the conversion rate of $\alpha(t, T, H)$ is stored at the temperature T and the humidity H for a period t is provided to the reaction model expressed by the formula 2 or the formula 3, and A, E and B and a parameter included in the reaction model are estimated. This enables extrapolation along the time axis, the temperature axis and the humidity axis in regard to the measurement data MD. In general, the higher the temperature and humidity, the faster the reaction. Therefore, it is possible to obtain the measurement data of a higher conversion rate in the same period by performing the stability test under the conditions of high temperature and high humidity. Thus, there is an advantage that the outline of a reaction model can be easily grasped in a short period.

Extrapolation along the time axis and the temperature axis may be performed with use of the normal Arrhenius equation shown in the formula 4 instead of the modified Arrhenius equation shown in the formula 1.

[Formula 4]

$$k(T) = A\exp\left(-\frac{E}{RT}\right) \tag{4}$$

An initial conversion rate $\alpha_0 = \alpha(0, T, H)$ may be set in advance, or an initial conversion rate $\alpha_0$ may be treated as an estimation parameter.

(3-4) Conversion from Peak Area to Conversion Rate

Next, conversion from a peak area to a conversion rate will be described. Although the measurement data MD is used as the conversion rate $\alpha(t, T, H)$ in the above-mentioned estimation processing, the actually obtained measurement data MD is often a peak area $\beta(t, T, H)$ of a substance obtained through liquid chromatography. As for a substance the amount of which is to "decrease" during a reaction process, such as an active ingredient, the reaction is considered complete when the substance is absent. That is, when it is assumed that the peak area for t=0 is $\beta_0$ (independent of temperature and humidity), a peak area can be converted into a conversion rate with use of the formula 5.

[Formula 5]

$$\alpha(t, T, H) = \frac{\beta_0 - \beta(t, T, H)}{\beta_0} \tag{5}$$

In case of prediction in regard to a substance the amount of which is to "increase" during a reaction process such as an impurity, further contrivance is required. In a case in which an amount of a substance increases, since the value of a peak area at which the reaction is considered complete is unknown, a peak area cannot be converted into a conversion rate. As such, a peak area for t=∞ is added to a reaction model as an estimation parameter $\beta_\infty$. With use of the estimation parameter $\beta_\infty$, the relationship between a peak area and a conversion rate is expressed by the formula 6.

[Formula 6]

$$\alpha(t, T, H) = \frac{\beta(t, T, H)}{\beta_\infty} \tag{6}$$

Here, it is assumed that $\beta_\infty$ does not change in accordance with the temperature or humidity. It is possible to construct an estimation model with a peak area as an input value by substituting the formula 5 or the formula 6 in the formula 2 or the formula 3.

For example, it is assumed that $g(\alpha)$ is expressed by the formula 7, and a reaction model is expressed by the D1 model shown in FIG. 4, that is, the formula 8. Thus, $\beta(t, T, H)$ is expressed by the formula 9 with use of the formulas 6 to 8. As shown in the formula 9, the parameters A, E and B are estimated, so that a peak area at any period of time can be estimated.

[Formula 7]

$$g(\alpha) = A\exp\left(-\frac{E}{RT} + B \times H\right)t \tag{7}$$

[Formula 8]

$$g(\alpha) = \alpha^2 \tag{8}$$

[Formula 9]

$$\beta(t, T, H) = \beta_\infty \sqrt{A\exp\left(-\frac{E}{RT} + B \times H\right)t} \tag{9}$$

(4) Estimation Method with Use of Similar Substances

Next, an analysis method with use of similar substances according to an embodiment will be described with reference to the flowchart of FIG. 6. The flowchart of FIG. 6 shows a process to be executed by the CPU 11 shown in FIG. 1. That is, the process is to be executed by each of the functions 21 to 24 shown in FIG. 2 when the CPU 11 runs the program P1 while using the hardware resources such as the RAM 12.

In the step S11, the acquirer 21 acquires quantitative measurement information of a plurality of substances including a test substance present in a sample. Specifically, the acquirer 21 acquires the measurement data MD in regard to a substance (an active ingredient or an impurity) included in a pharmaceutical. Here, the acquirer 21 acquires the measurement data MD in regard to a plurality of impurities included in a pharmaceutical, by way of example.

FIG. 7 is a diagram showing the profiles of a plurality of impurities J1 to J5 included in a pharmaceutical. In FIG. 7, the abscissa indicates the time, and the ordinate indicates a peak area. As shown in the diagram, the impurities J1, J4, J5 out of the plurality of impurities have similar reaction mechanisms. Thus, the impurities J1, J4, J5 are considered to have similar decomposition/production profiles. In the present specification, the substances having these similar decomposition/production profiles are referred to as "similar substances." In the present invention, the "similar substances" are utilized for estimation of a parameter of a reaction model of a specific test substance included in the "similar substances."

That the substances X1, X2, . . . , XN have a property as "similar substances" can be rephrased as that "the substances X1, X2, . . . , XN have a common conversion rate, and only coefficients (multiplication by constant) used for conversion from a conversion rate to a peak area differ for substances Xi." This property can further be rephrased as that "only a peak area for t=∞ differs among the substances Xi, and all of the parameters determining a conversion rate (the parameters A, E and B of the modified Arrhenius equation, a parameter n of a generalized reaction model, and the like) have a common value or a common distribution."

In FIG. 8, the substances X11, X12 are "similar substances," by way of example. As shown in the diagram, the profiles of the substances X11, X12 have a common conversion rate $\alpha 1$ and can be converted with use of constants $\beta_\infty^{(1)}$ and $\beta_\infty^{(2)}$.

The conversion rates of the substances Xi at each point in time, each temperature and each humidity are expressed by the formula 10, and the peak areas of the substance Xi at each point in time, each temperature and each humidity are expressed by the formula 11.

[Formula 10]

$$\alpha^{(i)}(t,T,H)(i=1,2, . . . ,N) \tag{10}$$

[Formula 11]

$$\beta^{(i)}(t,T,H)(i=1,2,\dots,N) \qquad (11)$$

Letting the peak areas of the substances Xi for t=∞ be $\beta_\infty^{(i)}$(i=1, 2, . . . , N), the relationship between a conversion rate and the peak area is provided by the formula 12. As described with reference to FIG. 8, the constant $\beta_\infty^{(i)}$ can be referred to as a conversion parameter for a conversion rate.

[Formula 12]

$$\alpha^{(i)}(t, T, H) = \frac{\beta^{(i)}(t, T, H)}{\beta_\infty^{(i)}} (i = 1, 2, \dots, N) \qquad (12)$$

Because the plurality of substances Xi are similar substances, a reaction model is common among the plurality of substances Xi and is expressed by the formula 13 or the formula 14.

[Formula 13]

$$f\left(\alpha^{(i)}(t, T, H)\right) = \frac{1}{A\exp\left(-\dfrac{E}{RT} + B \times H\right)} \frac{d\alpha}{dt} \qquad (13)$$

[Formula 14]

$$g\left(\alpha^{(i)}(t, T, H)\right) = A\exp\left(-\frac{E}{RT} + B \times H\right)t \qquad (14)$$

In this manner, it is possible to commonly use the measurement data MD of each of the substances Xi for the similar substances by modeling the plurality of substances Xi with use of a common reaction model. That is, the measurement data MD of the similar substances can also be used for estimation as compared to a case in which only the measurement data MD of a test substance is conventionally used for estimation. Since $\beta_\infty^{(i)}$(i=1, 2, . . . , N) is introduced instead of $\beta_\infty$, the number of estimation parameters is increased by (N−1). Further, in a case in which the posterior distribution of each estimation parameter of this model is obtained with use of Bayesian inference, since the substances $\beta_\infty^{(1)}$ and $\beta_\infty^{(2)}$ respectively have posterior distributions, the posterior distributions of the substances X11, X12 cannot always and immediately be converted with use of a specific value.

Next, in the step S12, the estimator 22 retrieves the reaction model ML stored in the storage device 16. As shown in FIGS. 1 and 2, a plurality of reaction models ML are stored in the storage device 16. For example, the reaction model ML such as the D1 model or a D2 model shown in FIG. 4 are stored in the storage device 16. The estimator 22 selects and retrieves the reaction model ML to be applied to a test substance from among the reaction models ML stored in the storage device 16. In the present embodiment, because a plurality of substances including a test substance are used as similar substances, the reaction model ML commonly applied to these similar substances is selected to be retrieved.

Subsequently, in the step S13, the estimator 22 models a test substance using the reaction model ML that is retrieved in the step S12. As such, the estimator 22 provides the measurement data MD (quantitative measurement information) of the plurality of substances which are the similar substances to the reaction model ML of the test substance to estimate a parameter and a conversion parameter of the reaction model ML. In this manner, the estimation method according to the present embodiment with which the quantitative measurement information of similar substances is utilized as the information common to the similar substances is referred to as a simultaneous estimation method. Here, the ratio of a peak area of each of a plurality of substances (a plurality of impurities) to a peak area of a main component (active ingredient) is provided to the reaction model ML of a test substance, so that a parameter of the reaction model ML is estimated. Although Bayesian inference is used here by way of example for estimation of a parameter, another regression analysis method such as a least squares method may be used.

Next, in the step S14, the calculator 23 calculates the quantitative estimation information of a test substance in any period of time based on a parameter of the reaction model estimated by the estimator 22. For example, the calculator 23 calculates a peak area, a peak area ratio and the like of the test substance in any period of time. Alternatively, the calculator 23 calculates a confidence interval or a quantile of the peak area or the peak area ratio of the test substance in any period of time. For example, the calculator 23 calculates the peak area ratio, a confidence interval of the peak area ratio or a quantile of the peak area ratio, the peak area ratio being a ratio of an impurity with respect to an active ingredient included in a pharmaceutical one year later, two years later, three years later or the like. The calculated quantitative estimation information of the test substance may be displayed on the display 15 by the outputter 24.

(5) Modified Example of Conversion from Peak Area to Conversion Rate

In the above-mentioned embodiment, a peak area is converted into a conversion rate is "only by multiplication by constant," by way of example. In a modified example, a peak area may be converted into a conversion rate by "multiplication by constant+addition by constant" or "addition by constant."

For example, in case of "multiplication by constant+ addition by constant", a parameter $s^{(i)}$ may be added, and the conversion between a peak area and a conversion rate may be performed with use of the formula 15. However, in this case, the number of estimation parameters increases by 2(N−1) as compared to estimation in regard to a single substance.

[Formula 15]

$$\alpha^{(i)}(t, T, H) = \frac{\beta^{(i)}(t, T, H) - s^{(i)}}{\beta_\infty^{(i)}} (i = 1, 2, \dots, N) \qquad (15)$$

Alternatively, with use of the formula 16, a substance the amount of which "decreases" such as an active ingredient can be included as a substance subject to simultaneous simulation of a substance the amount of which "increases" such as an impurity.

[Formula 16]

$$\alpha^{(i)}(t, T, H) = \frac{\beta_0 - \beta^{(i)}(t, T, H)}{\beta_0 - \beta_\infty^{(i)}} \qquad (16)$$

$\beta_\infty$ may be a constant such as 0, or may be treated as an estimation parameter in view of the possibility that the reaction ends before all of the substances are decomposed. Therefore, this estimation is not limited to the data of impurities, and it is possible to perform simultaneous estimation with use of the data of a plurality of active ingredients or the data of a combination of an active ingredient and an impurity. Although the value for β(t, T, H) is used as a peak area here, the same applies to a case in which a quantitative value of a test substance such as a peak area ratio with respect to the peak of an active ingredient is obtained.

(6) Similar Substances

As described above, that the substances X1, X2, . . . , XN have a property as "similar substances" can be rephrased as that "the substances X1, X2, . . . , XN have a common conversion rate, and only coefficients (multiplication by constant, addition by constant, multiplication by constant+addition by constant, and the like) used for conversion from a conversion rate to a peak area differ for the substances Xi." That is, a plurality of substances can be used as "similar substances" in a case in which having conversion rates that are close to one another. Whether the conversion rates are close to one another can be determined based on the past experimental data or the like. Alternatively, it can be rephrased as that the temporal change of quantitative measurement information of each substance in a plurality of substances can be converted by affine transformation. Further, a plurality of substances can be used as "similar substances" in a case in which parameters obtained when the plurality of substances are modeled with use of the same reaction model are close to one another. In other words, a plurality of substances can be used as "similar substances" in a case in which the parameters estimated by regression are close to one another when respective substances are modeled with use of the same reaction model. Furthermore, that a plurality of substances can be used as "similar substances" can be rephrased as that quantitative measurement information of one substance included in a plurality of substances can be expressed by a function in which quantitative measurement information of another substance included in the plurality of substances is used as a variable.

An example in which a plurality of substances can be used as "similar substances" includes a case in which a plurality of substances are a group of substances produced by an oxidation reaction. As another example in which a plurality of substances can be used as "similar substances" includes a case in which a plurality of substances are a group of substances produced by a hydrolysis reaction.

The simultaneous estimation method according to the present embodiment can be used for an analysis of a formulation or a drug substance, for example. At this time, it is possible to estimate a parameter of a reaction model with high accuracy by using a plurality of substances (active ingredients or impurities) included in a formulation or a drug substance as similar substances. The methods of grouping a plurality of impurities included in a formulation or a drug substance as similar substances include a method of determining whether the curves of a conversion rate are resembling one another and a method of determining the correlation in regard to the curves of a conversion rate, for example. Further, an experiment may be performed after impurities are classified according to a condition such as an oxidation condition, an acidic condition or a hydrolysis condition, and the like, and the correlation in regard to a conversion rate, and the like, may be determined. It is preferable that a substance that is burned or deliquesced in a reaction process is not included as similar substances as a substance having another reaction mechanism.

(7) Results of Simulation

Next, the results of simulation obtained by simultaneous estimation of the present invention will be shown. FIG. 9 is a diagram showing the simulation data. This simulation data is the data obtained when impurities of a Silodosin formulation are simulated under the condition of 25° C. and 60% RH (Relative Humidity). Specifically, the simulation data represents the peak area ratios of five impurities J11 to J15 with respect to the peak of an active ingredient. At this time, in the simulation, it is assumed that the impurities have a common conversion rate, and the conversion rate can be converted by "multiplication by constant+addition by constant."

FIG. 10 shows the simulation data SD obtained as a result of simulation of actual measurement data in regard to the impurities of a Silodosin formulation obtained by addition of Gaussian noise to the simulation shown in FIG. 9. Similarly to FIG. 9, FIG. 10 also shows the peak area ratios of the five impurities J11 to J15 with respect to the peak of the active ingredient. FIG. 10 shows the simulation of the data obtained by measurement in regard to each impurity under six combined conditions of a temperature and humidity at 11 points in time. The conditions of a temperature and humidity used for simulation includes 6 combinations such as 60° C. and 50% RH, or 80° C. and 10% RH. FIG. 11 is a diagram showing the data that is obtained when the data obtained under a single condition of 60° C. and 50% RH is extracted from the simulation data SD shown in FIG. 10. In case of estimation with use of the data of a single impurity, even when six combined conditions of temperature and humidity are used at 11 points in time, only data for 66 points can be used. In contrast, with the simultaneous estimation method with use of similar substances in the present invention, five impurities are utilized as similar substances, so that the data of 330 points, which is five times as much as that of the other method, can be used.

FIG. 12 is a diagram showing a result of simulation obtained by the simultaneous estimation method according to the present embodiment with use of the simulation data SD shown in FIG. 10. FIG. 12 shows the predicted temporal change in regard to each impurity at 25° C. and 60% RH. In FIG. 12, TR indicates the true peak area ratio of the simulation data SD. RE1 represents a result of estimation, of the peak area ratio of each impurity included in similar substances with use of Bayesian inference, with use of the data of five impurities used as similar substances included in the simulation data SD. RE1 indicates a 95% confidence interval of the peak area ratio of each impurity. Further, CE1 indicates the median value of the peak area ratio of each impurity.

In contrast, RE2 indicates a result of estimation, of the peak area ratio of each impurity with use of Bayesian inference, with use of the data of a single impurity included in the simulation data SD. RE2 indicates a 95% confidence interval of the peak area ratio of each impurity. Further, CE2 indicates the median value of the peak area ratio of each impurity. In this manner, it can be seen that the simultaneous estimation model obtained with utilization of similar substances in the present embodiment provides more accurate confidence intervals than the conventional estimation model in regard to most impurities and points in time.

(8) Modified Example

In the above-mentioned first embodiment, the calculator 23 calculates quantitative estimation information of a test substance in any period of time based on a parameter estimated by the estimator 22. In a modified example of the present embodiment, the information in regard to a period of time until the quantitative estimation information of a test substance reaches a predetermined threshold value is calculated.

FIG. 13 is a flowchart according to the modified example. The steps S21, S22 and S23 are similar to the steps S11, S12 and S13 described with reference to FIG. 6. In the step S21, the acquirer 21 acquires measurement data MD of a substance included in a pharmaceutical. In the step S22, the estimator 22 retrieves a reaction model ML from the storage device 16. In the step S23, the estimator 22 provides the quantitative measurement information of a plurality of substances to the reaction model ML of the test substance to estimate a parameter and a conversion parameter of the reaction model ML.

In the step S24, the calculator 23 calculates the information in regard to a period of time until the quantitative estimation information of the test substance reaches a predetermined threshold value based on a parameter estimated by the estimator 22. For example, the calculator 23 calculates the number of days (a period of time) until the peak area ratio of an impurity reaches the predetermined threshold value. Alternatively, the calculator 23 calculates a confidence interval or a quantile in regard to the number of days (a period of time) until the peak area ratio of an impurity reaches the predetermined threshold value. Thus, in a case in which the allowable value of the peak area ratio of an impurity of a pharmaceutical is defined, a confidence interval or a quantile in regard to an effective shelf-life of a pharmaceutical can be presented.

(9) Other Modified Examples

In each above-mentioned embodiment, the sample analysis device 1 is a pharmaceutical analysis device, by way of example. The sample analysis device 1 of the present embodiment can be utilized to acquire quantitative estimation information of a test substance in various samples other than pharmaceuticals. The list of reaction models shown in FIG. 4 is one example. A reaction model to which the analysis method in the present embodiment is applied is not limited in particular.

The above-mentioned sample analysis device 1 can estimate a parameter of a reaction model with high accuracy by using a plurality of substances (active ingredients, impurities or the like) as similar substances. The sample analysis device 1 can calculate the quantitative estimation information in regard to each of the plurality of substances with use of such characteristics of the present embodiment. Then, the plurality of substances may be automatically sorted based on the quantitative estimation information calculated in regard to each of the plurality of substances. Alternatively, the sample analysis device 1 can calculate a period of time until the quantitative estimation information reaches a predetermined threshold value in regard to each of the plurality of substances. Further, the plurality of substances may be automatically sorted based on a period of time calculated in regard to each of the plurality of substances.

(10) Aspects

It will be appreciated by those skilled in the art that the exemplary embodiments described above are illustrative of the following aspects.

(Item 1) A sample analysis device according to one aspect includes an acquirer that acquires quantitative measurement information of a plurality of substances including a test substance present in a sample, an estimator that retrieves a reaction model stored in a storage device, models the test substance using the reaction model and provides the quantitative measurement information of the plurality of substances to the reaction model of the test substance to estimate a parameter of the reaction model, and a calculator that calculates quantitative estimation information of the test substance in any period of time or information in regard to a period of time until quantitative estimation information of the test substance reaches a predetermined threshold value, based on the parameter estimated by the estimator.

A parameter of the reaction model can be estimated with high accuracy.

(Item 2) The sample analysis device according to item 1, wherein the plurality of substances may be sorted by calculation of quantitative estimation information in regard to each of the plurality of substances or information in regard to a period of time until quantitative estimation information in regard to each of the plurality of substances reaches a predetermined threshold value by the calculator.

Substances can be sorted based on highly accurate estimation.

(Item 3) The sample analysis device according to item 2, wherein the plurality of substances may be a group of substances to be selected from the group consisting of a group of substances having the close parameters that are obtained when the reaction model is modelled, a group of substances having close conversion rates, a group of substances in regard to which each substance has quantitative measurement information a temporal change of which is convertible by affine transformation, a group of substances in regard to which the quantitative measurement information of one substance included in the plurality of substances is expressible by a function with the quantitative measurement information of another substance included in the plurality of substances used as a variable, a group of substances produced by an oxidation reaction and a group of substances produced by a hydrolysis reaction.

Quantitative measurement information can be utilized among the substances having common characteristics.

(Item 4) The sample analysis device according to item 1, wherein a plurality of reaction models may be stored in the storage device.

An appropriate reaction model to be applied to a test substance can be selected from among the plurality of reaction models.

(Item 5) The sample analysis device according to item 1, wherein the quantitative estimation information may include a quantitative value, a confidence interval or a quantile of a test substance in any period of time.

Quantitative estimation information of a sample in any period of time can be provided to a user.

(Item 6) The sample analysis device according to item 1, wherein the information in regard to a period of time may include a period of time, a confidence interval or a quantile until the quantitative estimation information of the test substance reaches a predetermined threshold value.

Information such as the validity period of a sample can be provided to the user.

(Item 7) A sample analysis method according to another aspect includes acquiring quantitative measurement information of a plurality of substances including a test substance present in a sample, retrieving a reaction model stored in a storage device, modeling the test substance using the reaction model and providing the quantitative measurement information of the plurality of substances to the reaction model of the test substance to estimate a parameter of the reaction model, and calculating quantitative estimation information of the test substance in any period of time or information in regard to a period of time until quantitative estimation information of the test substance reaches a predetermined threshold value, based on the estimated parameter.

A parameter of the reaction model can be estimated with high accuracy.

(Item 8) The sample analysis method according to item 7, may include sorting the plurality of substances by calculating quantitative estimation information in regard to each of the plurality of substances or information in regard to a period of time until quantitative estimation information in regard to each of the plurality of substances reaches a predetermined threshold value in the calculating.

Substances can be sorted based on highly accurate estimation.

(Item 9) The sample analysis method according to item 8, wherein the plurality of substances may be a group of substances to be selected from the group consisting of a group of substances having the close parameters that are obtained when the reaction model is modelled, a group of substances having close conversion rates, a group of substances in regard to which each substance has quantitative measurement information a temporal change of which is convertible by affine transformation, a group of substances in regard to which the quantitative measurement information of one substance included in the plurality of substances is expressible by a function with the quantitative measurement information of another substance included in the plurality of substances used as a variable, a group of substances produced by an oxidation reaction and a group of substances produced by a hydrolysis reaction.

Quantitative measurement information can be utilized among the substances having common characteristics.

(Item 10) A pharmaceutical analysis device according to another aspect, wherein the sample may include a formulation or a drug substance, and the test substance may include an active ingredient or an impurity present in the formulation or the drug substance, in the sample analysis device according to item 1.

A parameter of a reaction model can be estimated with high accuracy in an analysis of a pharmaceutical.

(Item 11) A pharmaceutical analysis method according to another aspect, wherein the sample may include a formulation or a drug substance, and the test substance may include an active ingredient or an impurity present in the formulation or the drug substance, in the sample analysis method according to item 7.

A parameter of a reaction model can be estimated with high accuracy in an analysis of a pharmaceutical.

While preferred embodiments of the present disclosure have been described above, it is to be understood that variations and modifications will be apparent to those skilled in the art without departing the scope and spirit of the present disclosure. The scope of the present disclosure, therefore, is to be determined solely by the following claims.

We claim:

1. A sample analysis device for estimating an amount of a product or a period for a target amount, the sample analysis device comprising:

an apparatus configured to measure amounts of a plurality of substances in a sample of the product, the amounts comprising quantitative measurement information of the plurality of substances;

a controller implemented by execution of a program by a processor using a memory, the controller comprising:

an acquirer that measures the plurality of substances including a test substance present in the sample, and acquires a first measurement value and a second measurement value of the test substance, wherein the first measurement value and the second measurement value are values acquired at different times;

an estimator that retrieves a reaction model describing a chemical reaction of the test substance, and estimating a reaction rate constant of the reaction model by inputting the first measurement value and the second measurement value into the reaction model;

a calculator that calculates an estimated amount of the test substance in any period of time using the reaction model, or a period of time until the test substance reaches an arbitrary amount using the reaction model;

a display that indicates the estimated amount or the period of time.

2. The sample analysis device according to claim 1, wherein the plurality of substances are sorted by calculation of quantitative estimation information in regard to each of the plurality of substances or information in regard to a period of time until quantitative estimation information in regard to each of the plurality of substances reaches a predetermined threshold value by the calculator.

3. The sample analysis device according to claim 2, wherein the plurality of substances are a group of substances to be selected from the group consisting of a group of substances having close parameters that are obtained when the reaction model is modelled, a group of substances having close conversion rates, a group of substances in regard to which each substance has quantitative measurement information a temporal change of which is convertible by affine transformation, a group of substances in regard to which the quantitative measurement information of one substance included in the plurality of substances is expressible by a function with the quantitative measurement information of another substance included in the plurality of substances used as a variable, a group of substances produced by an oxidation reaction and a group of substances produced by a hydrolysis reaction.

4. The sample analysis device according to claim 1, wherein a plurality of reaction models are stored in a storage device.

5. A pharmaceutical analysis device, wherein the sample includes a formulation or a drug substance, and the test substance includes an active ingredient or an impurity present in the formulation or the drug substance, in the sample analysis device according to claim 1.

6. The sample analysis device of claim 1, wherein the period is a period in which the value of an active ingredient of the product is in a reference range or the value of an impurity in the product is equal to or smaller than a reference value.

7. A sample analysis method for estimating an effective period of use of a product, the sample analysis method including:

measuring amounts of a plurality of substances in a sample of the product, including acquiring a first measurement value and a second measurement value of a test substance in the sample, wherein the first measurement value and the second measurement value are values acquired at different times;

retrieving a reaction model from a storage device, the reaction model describing a chemical reaction of the test substance, and estimating a reaction rate constant of the reaction model by inputting the first measurement value and the second measurement value into the reaction model;

calculating an estimated amount of the test substance in any period of time using the reaction model, or a period of time until the test substance reaches an arbitrary amount using the reaction model; and determining the effective period of use of the product based on the calculation.

8. The sample analysis method according to claim 7, including sorting the plurality of substances by calculating quantitative estimation information in regard to each of the plurality of substances or information in regard to a period of time until quantitative estimation information in regard to each of the plurality of substances reaches a predetermined threshold value in the calculating.

9. The sample analysis method according to claim 8, wherein the plurality of substances are a group of substances to be selected from the group consisting of a group of substances having the close parameters that are obtained when the reaction model is modelled, a group of substances having close conversion rates, a group of substances in regard to which each substance has quantitative measurement information a temporal change of which is convertible by affine transformation, a group of substances in regard to which the quantitative measurement information of one substance included in the plurality of substances is expressible by a function with the quantitative measurement information of another substance included in the plurality of substances used as a variable, a group of substances produced by an oxidation reaction and a group of substances produced by a hydrolysis reaction.

10. A pharmaceutical analysis method, wherein the sample includes a formulation or a drug substance, and the test substance includes an active ingredient or an impurity present in the formulation or the drug substance, in the sample analysis method according to claim 7.

11. The method of claim 7, wherein the effective period of use is a period in which the value of an active ingredient of the product is in a reference range or the value of an impurity in the product is equal to or smaller than a reference value.

12. A sample analysis method for estimating an effective period of use of a product, the sample analysis method including:

measuring amounts of a plurality of substances in a sample of the product, the amounts comprising quantitative measurement information of the plurality of substances;

acquiring the quantitative measurement information of the plurality of substances including a test substance present in the sample;

retrieving a reaction model stored in a storage device;

modeling the test substance using the reaction model and providing the quantitative measurement information of the plurality of substances to the reaction model of the test substance to estimate a parameter of the reaction model;

calculating quantitative estimation information of the test substance for a plurality of periods of time until quantitative estimation information of the test substance reaches a predetermined threshold value, based on the estimated parameter; and determining the effective period of use of the product based on a period of time associated with the reaching of the predetermined threshold value.

13. The sample analysis method of claim 12, wherein the product is a pharmaceutical product, and the effective period of use is a period in which the value of an active ingredient of the product is in a reference range or the value of an impurity in the product is equal to or smaller than a reference value.

14. The sample analysis method of claim 13, wherein the parameter is a reaction rate constant.

15. The sample analysis method of claim 13, wherein the test substance includes an active ingredient or an impurity present in the pharmaceutical product.

* * * * *